(12) United States Patent  (10) Patent No.: US 8,110,346 B2
Bussolati  (45) Date of Patent: Feb. 7, 2012

(54) PROCESS FOR PRESERVING TISSUES

(75) Inventor: Giovanni Bussolati, Turin (IT)

(73) Assignee: Milestone S.r.l. (IT)

( * ) Notice: Subject to any disclaimer, the term of this patent is extended or adjusted under 35 U.S.C. 154(b) by 225 days.

(21) Appl. No.: 12/331,107

(22) Filed: Dec. 9, 2008

(65) Prior Publication Data

US 2009/0191533 A1  Jul. 30, 2009

(30) Foreign Application Priority Data

Dec. 13, 2007  (EP) ..................................... 07123113

(51) Int. Cl.
*A01N 1/00*  (2006.01)
(52) U.S. Cl. ......................... 435/1.1; 435/284.1; 27/24.1
(58) Field of Classification Search ................... 435/1.1, 435/284.1; 27/24.1
See application file for complete search history.

(56) References Cited

U.S. PATENT DOCUMENTS

| 5,187,917 | A | * | 2/1993 | Mykleby .......................... 53/434 |
| 5,216,789 | A |   | 6/1993 | Pomares et al. |
| 5,659,933 | A |   | 8/1997 | McWilliams |
| 5,715,583 | A | * | 2/1998 | Sandoval ........................... 27/11 |
| 6,739,112 | B1 |  | 5/2004 | Marino |

FOREIGN PATENT DOCUMENTS

| DE | 10155368 A1 | 5/2003 |
| WO | 92/11760 A1 | 7/1992 |
| WO | 02/18210 A1 | 3/2002 |

OTHER PUBLICATIONS

Church et al., "Modified atmosphere packaging technology: a review," J Sci Food Agric 67:143-152, 1995.*
CVP® Systems, Fresh Vac® Modified Atmosphere Packaging Machine, A-200, http://www.cvpsystems.com/models/a200.htm printed from the Internet on Sep. 20, 2011.*
CVP® Systems, Fresh Vac® Modified Atmosphere Packaging Machine, A-200, brochure, http://www.cvpsystems.com/models/CVP_PDF/A-200.pdf, printed from the Internet on Sep. 20, 2011.*
The European Search Report issued in connection with EP 07123113.8-1257 on Mar. 5, 2008.

* cited by examiner

*Primary Examiner* — Rosanne Kosson
(74) *Attorney, Agent, or Firm* — The H.T. Than Law Group

(57) ABSTRACT

A process for preserving tissues is described which comprises transferring the tissues in a container and evacuating the container.

8 Claims, 4 Drawing Sheets

PROCESS FOR PRESERVING TISSUES

BACKGROUND OF THE INVENTION

1. Technical Field

This invention relates to the field of preservation of tissues after removal by surgery for preserving the tissues for subsequent histopathological examination and tissue banking as well as for transplantation of scientific purposes.

2. Description of the Background Art

The standard use of formalin (formaldehyde), both as a preserver and fixative for histological processing, is encountering increasing criticisms because of toxicity and environmental concerns. Moreover, the declaration recently issued by the International Agency for Research on Cancer, (International Agency for Research on Cancer (2006), Monographs on the evaluation of Carcinogenic Risk to humans. (IARC, Vol. 88) Lyon, France), which classified formaldehyde as a Class 1 carcinogen has definitely increased the request by health authorities, technicians and practicing pathologists to entirely avoid or at least substantially reduce contact with formalin. Such requests contrast with the considerable advantages offered by this reliable fixative. Although it should be acknowledged that in modern pathology laboratories visitors are not any more confronted with the vapors of a strong scent, since formalin processing is mostly carried out under aspiration hoods, a critical passage is still existent due to the transfer of tissues from the surgical theatre to the pathology lab. Apart from small biopsies which are directly collected into pre-filled containers and cause no concerns, problems are encountered with the immersion of large specimens and organs into large boxes to be filled with formalin.

Such problems may be summarized as follows:
1) Plastic containers are large and relatively heavy while on occasion spilling may occur.
2) Immersion into formalin prevents the collection of fresh material for tissue banking. Fixation starts, but only at the periphery. Discoloration occurs while a delay in the transfer to pathology labs is somehow justified by the fact that "the tissue is already in formalin".
3) Nurses at the surgical theatre become increasingly concerned for toxicity and cancerogenicity issues since the fluid has to be managed freely and not under hood.
4) When the container arrives at the pathology lab, its opening, removal of the specimen and reduction of the latter constitutes a major cause of diffusion of formaldehyde vapors.

In more recent years, alternatives to formalin (formaldehyde) have been proposed. From WO 2004/093541 A1 a formaldehyde-free, non-alcoholic tissue preservative composition is known which comprises ethanedial and a polar aprotic solvent in aqueous solution. Further known tissue preservatives compositions which do not contain formalin, contain glutaraldehyde or alcoholic solvents or compounds such as acetic acid which pose hazardous waste disposal problems and potentially are irritants to persons exposed to tissue preservative compositions in their work.

It is object of the invention to provide a technology to satisfactorily preserve human and animal tissues after removal from the body to prevent the growth and propagation of microbes and autolytic processes without the need of using tissue preserving agents which are toxic and environmentally hazardous and thus absolutely dangerous for people directly involved in resection, transplantation and examination of tissues.

SUMMARY OF THE INVENTION

The present invention provides a process for preserving tissues which comprise transferring the tissues in a container and evacuating the container.

Also disclosed is a vacuum device for preserving tissues after surgery comprising a vacuum chamber, a vacuum pump, an electrical controller, electrical valves for air and gas control and a thermosealer.

The tissues to be preserved are preferably tissues removed by surgical intervention. The process of the present invention is preferably applicable to tissues of human and animal origin.

The tissues. preserved according to the process of the present invention can be advantageously store d and transported for histopathological examination, transplantation and tissue banking.

Further fields of application are storing and transporting of partially formalin fixed tissues such as biopsy material. Anatomic specimens for scientific demonstration purposes can be also treated according to the process of the present invention which would avoid the permanent preservation in formalin.

BRIEF DESCRIPTION OF THE DRAWINGS

The figures are to illustrate the present invention.

DETAILED DESCRIPTION OF THE PREFERRED EMBODIMENTS

The process of the present invention is based on the principle that the tissues removed from the human or animal body are preserved by keeping them under vacuum, i.e. in an evacuated closed environment.

In principle, any tissue, tissue material or tissue specimen material may be used in the process of the present invention. Examples of the tissues are whole organs such as gallbladder, spleen, kidney, colon, thyroid, breast, etc. as well as cardiac vessels. Tissue materials can comprise parts of organs such as tumors and biopsy material.

The tissue material is removed by surgery from the human or animal body to transfer it in a container which can be tightly closed and should have a certain degree of flexibility. The size of the container is dependent on the size of the tissue material to be preserved. In a preferred embodiment of the process of the present invention, a plastic bag is used as a container.

The tissues can be transferred in a condition of either fresh or partially fixed.

The tissues can be transferred in a condition of either fresh or partially fixed.

Figure 1:
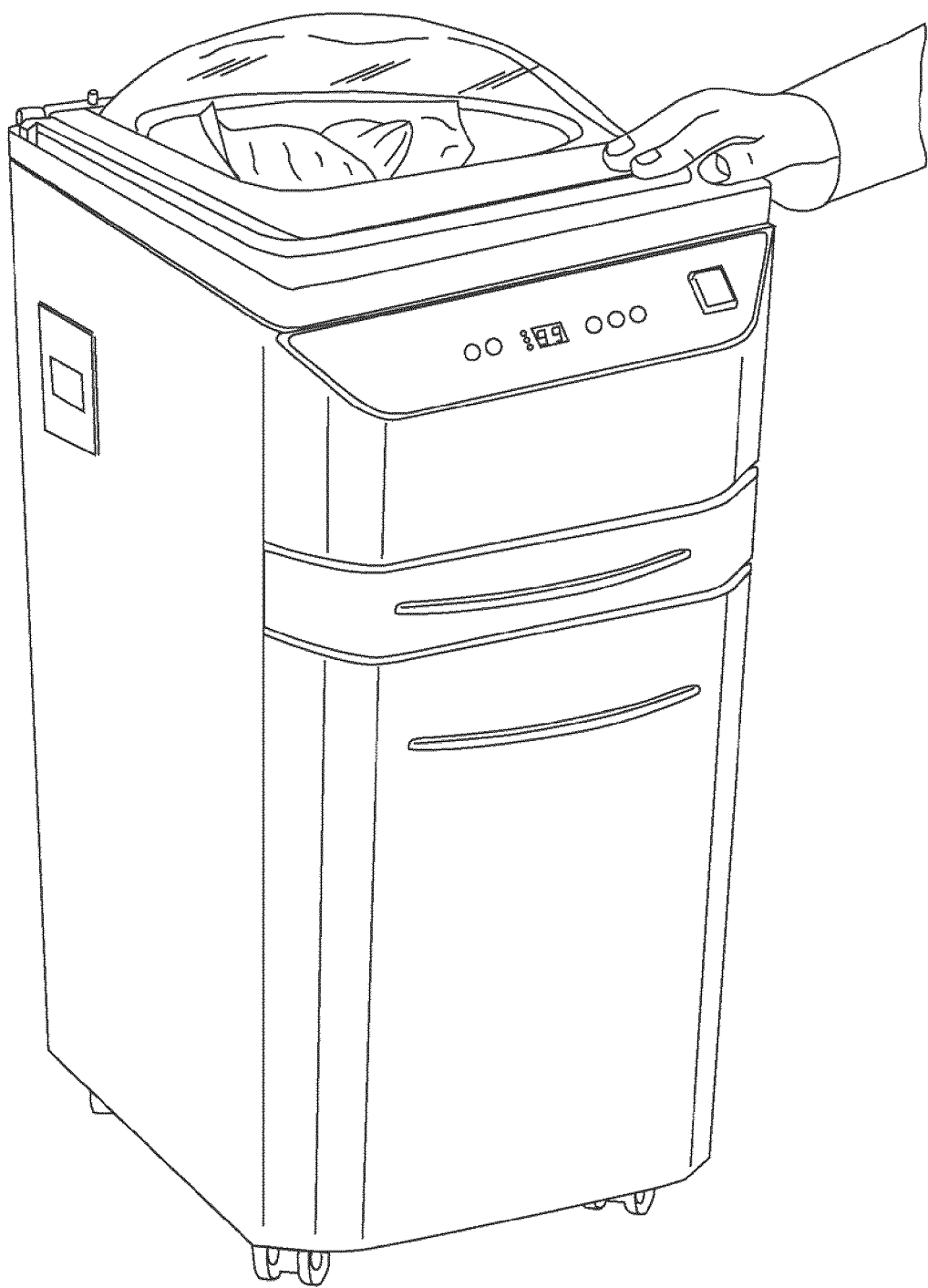
FIG. 1 shows an example of a vacuum device for carrying out the process of the present invention.

The evacuating of the tissues or tissue specimen material can be carried out in a vacuum device having sufficient volume to handle large containers. FIG. 1 shows an example of this vacuum device which can be easily transferred to a surgical theatre where it can be conveniently put into use by the personnel involved such as surgeons and nurses.

The surgical specimens are transferred in the container immediately after removal. For identification of the tissue specimens the container itself may have an identification label or, alternatively, an identification label can be attached to the surface of the container later on. The container filled with the tissue specimen is transferred to the vacuum device where the specimens in the containers are evacuated and sealed.

Usually, evacuating and sealing the containers in the vacuum device does. not take more than 30 seconds, a time range of approximately 15 seconds being more preferred. The sealed evacuated container filled with the tissue specimen is then removed from the vacuum device and stored in a refrigerator for a time period of a few hours up to 9.0 hours. Usually, the tissue specimen under vacuum is transferred to the pathology laboratory or to another surgery theatre as soon as possible, however, on rare occasions, the under vacuum tissues can be kept in the refrigerator at refrigerator temperatures at 4° C. for 1 day to 1 week (or more).

The evacuation of the container containing the tissue specimens is preferably carried out by reducing the pressure to at least below 100 mbar (10 kPa) in the vacuum device. More. preferred, the pressure is reduced within the range of 30-0 mbar (3 to 0 kpa).

Figure 2:
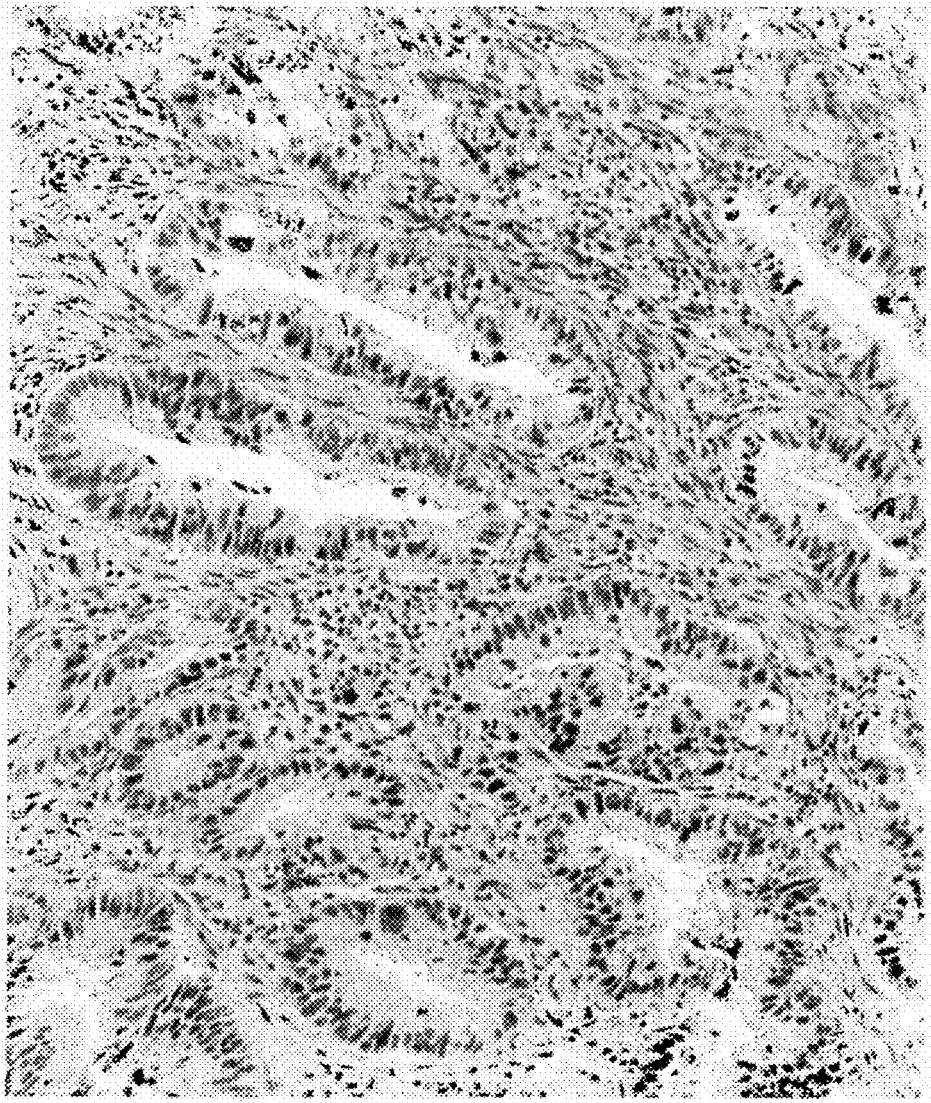
FIG. 2 shows a microscopic picture of a section of an adenocarcinoma of the colon which has been preserved according to the process of the present invention and then subjected to formalin fixation and paraffin embedding.

Once the tissue specimens under vacuum have reached their destination point, the specimens are removed from the containers and available for further processing. For histopathological examination, selected tissue blocks are inserted into cassettes for routinary fixation in formalin and paraffin embedding. FIG. 2 shows a microscopic tissue section of an adenocarcinoma of the colon which has been preserved according to the method of the present invention. The tissue specimen has been kept under vacuum for 4° C. for 48 hours, then routinely processed with formalin fixation and paraffin embedding. The structure is absolutely preserved and diagnosis is readily feasible.

Figure 3:
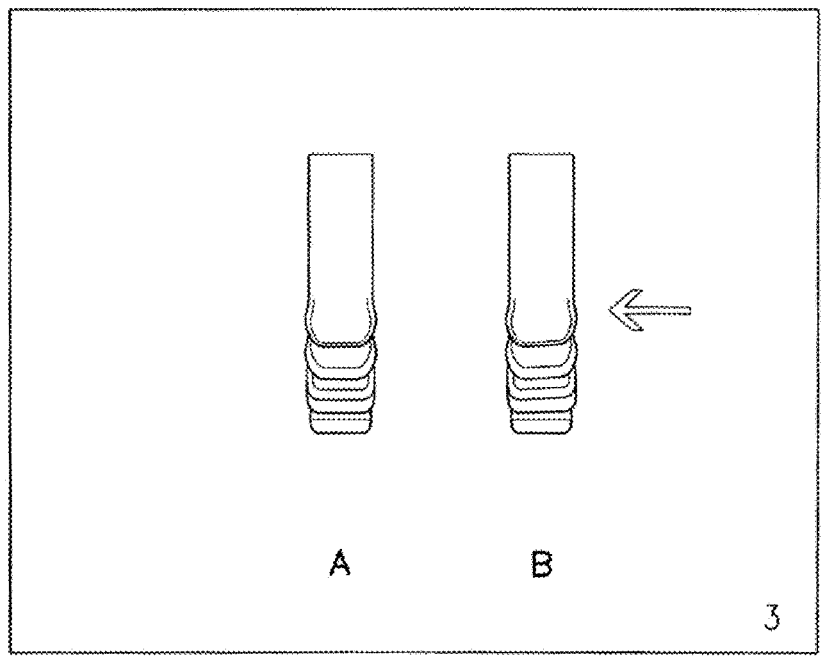
FIG. 3 shows the agarose gel chromatogram (1%) separation of extracted total RNA of colon mucosa either frozen immediately after removal (lane A) or preserved according to the process of the present invention (lane B).
Figure 4:
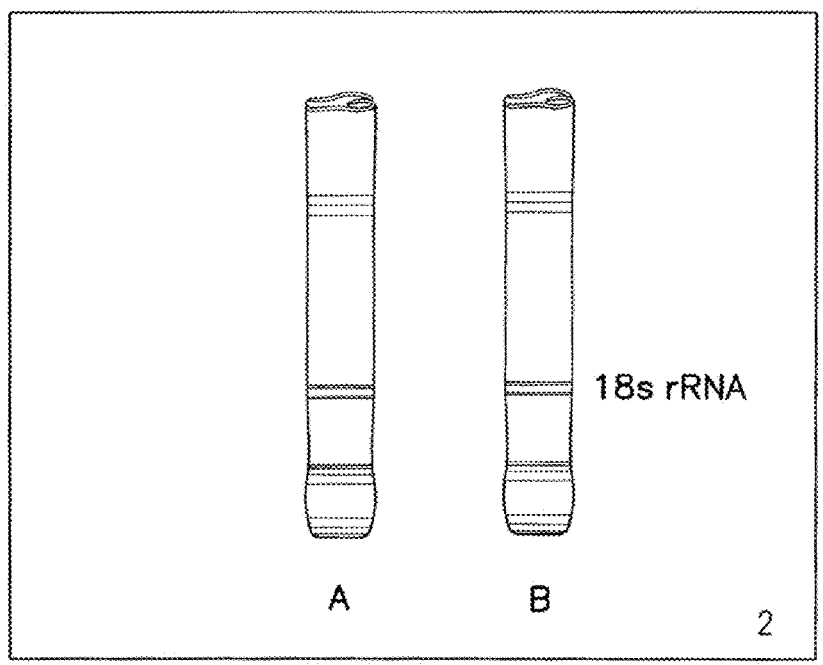
FIG. 4 shows a 1%. denaturing agarose gel of a total RNA running from colon mucosa with lanes A and B as described above showing an intact 18s rRNA band after preservation. of the RNA according to the process of the present invention.

The process of the present invention involving the under vacuum treatment of tissues and tissues specimen routinely also provides excellent material for tissue banking. The quality of RNA preservation is correlated with the time of treatment but it has been shown that tissues under vacuum kept in the refrigerator for a long time provide nucleic acids of highly acceptable quality. FIGS. 3 and 4 show agarose gel chromatograms (1%) of colon mucosa RNA at two different stages: lane A=tissue sample is frozen immediately after removal and lane B=tissue specimen preserved according to the process of the present invention and stored at 4° C. for 48 hours. The extracted RNA is of acceptable and similar quality. In FIG. 4 the 18s rRNA band is visible without any degradation seen. FIG. 3 represents RT-PCR products of cytoceratine 20 mRNA of different base pair number. The upper band indicated by an arrow is related to a 716 bp product.

The process of the present invention is also applicable to partially formalin fixed tissue. Tissues such as. biopsy material is preliminarily formalin fixed for a few hours and then subjected to the process according to the present invention to be kept under vacuum.

The rest of the specimen which is not intended for further use, is kept under formalin in sealed boxes as a reserve.

In an alternative embodiment of the process of the present invention, a protective atmosphere can be generated in the container in order to achieve a prolonged preservation of the tissue specimens.

For this purpose, the tissues are kept in a protective gas atmosphere using any medical gas or gas mixture suitable for preserving tissue samples. Preferably, an $N_2/CO_2$ gas mixture is used.

Figure 5:
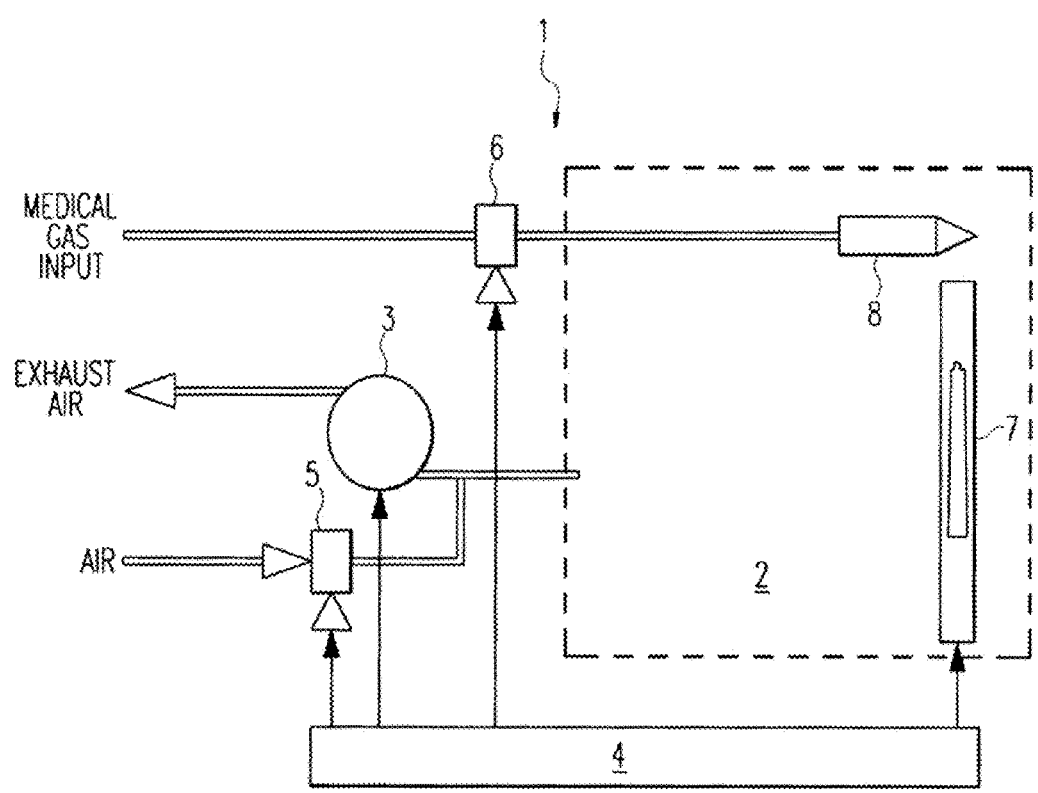
FIG. 5 schematically illustrates the functioning of the vacuum device as shown in FIG. 1.

As an example of providing a protective atmosphere in the container filled with the tissue specimen, the medical gas or gas mixture is introduced in the vacuum device when the minimum vacuum level is achieved in the vacuum chamber. Advantageously, there is no mechanical operation required. The pressure difference between the medical gas pressure which is maximum 3 bar and the container inside the vacuum chamber corresponding to the vacuum pressure is enough to inflate the container. A suitable vacuum device is for example a semi-professional device functioning as schematically shown in FIG. 5. The device 1 comprises the following technical means: a vacuum chamber 2, a vacuum pump 3, an electrical controller 4, electrical valves 5; 6 for air and gas control and a thermosealer 7.

The vacuum device 1 may be run as follows: The operator places the container, for example a plastic bag, with the tissue specimen inside in the vacuum chamber 2. The open side of the plastic bag is positioned over the thermosealer 7. The vacuum chamber 2 is then manually or automatically closed by a top lid (not shown). An electrical controller 4 activates the vacuum pump 3 to reduce the pressure inside the vacuum chamber 2. The top lid is kept in position by the difference of pressure. The vacuum chamber pressure is sequentially reduced from ambient pressure $10^5$ Pa (1 bar) to the minimum pressure. By the electrical controller 4 it is possible to select the desired vacuum level. Conveniently, the pressure is reduced to at least below 100 mbar (10 kPa), preferably below 30 mbar (3 kPa).

When it is desired to generate a protective atmosphere in the plastic bag, a medical gas or medical gas mixture is introduced into the vacuum chamber 2. When the minimum vacuum level is reached in the vacuum chamber 2, the medical gas is introduced through an electrical valve line 6. For introducing the medical gas directly in the plastic bag, a nozzle 8 is provided in the vacuum chamber.

As a final step, the system of the device 1 warms up a thermosealer 7 to seal the bag. Subsequently, the device 1 releases the vacuum to open the top lid to remove the evacuated sealed bag with the tissue specimen inside.

It has been shown that the process of the present invention provides for an excellent morphological preservation of the tissues while the immunohistochemical reactivity is fully maintained. The process of the present invention reduces the consumption of formalin to zero which is very well accepted especially by the personnel who was previously always confronted with heavy formalin vapors.

The process of the present invention also provides for excellent material for tissue banking. It has been shown that tissues kept in the refrigerator under vacuum provide nucleic acids of good quality.

The process of the present invention is highly environmentally save and meets the requests of health authorities and assists in avoiding exposure to hazardous formaldehyde. The absence of air essentially prevents autolytic processes, favors the cooling of the tissue specimens and provides relatively small and light containers filled with the evacuated specimens which are easy to carry or send by post compared to the highly heavy formalin filled containers of the prior art.

EXAMPLES

The following examples illustrate various specific aspects of the present invention and only serve to further illustrate the present invention.

Example 1

A colectomy specimen comprehensive of a colon cancer immediately after operation was introduced in a plastic bag and preserved under vacuum in a vacuum device Model VAC 10, Milestone, Bergamo, Italy. The vacuum applied was 100 mbar (10 kPa). A specimen of such tissue (approximately 1 square cm large) was removed from the tumor and put again under vacuum using the above procedure. It was then kept in a refrigerator at 4° C. for 82 hours. It was then immersed into formalin and processed using the routinary histological processing. Tissue sections were stained with haematoxylin and eosin. The histological structure appeared well preserved so that a correct diagnosis of adenocarcinoma of the colon could be made (FIG. 2).

As a control, a similar specimen was immersed into buffered saline and after 82 hours processed for histological examination. In such tissue, the structure was damaged because of autolytic processes.

Example 2

A colectomy specimen comprehensive of a colon cancer immediately after operation was preserved under vacuum as described in example 1. A specimen of such tissue (approximately 1 square cm large) was removed from the tumor and put again under vacuum using the above procedure. It was then kept in a refrigerator at 4° C. for 82 hours. It was further processed for RNA extraction. The RNA obtained was entirely intact as is shown in FIG. 3 and 4.

The invention claimed is:

1. A process for preserving a tissue, wherein the tissue to be preserved is selected from the group consisting of whole organs, parts of organs, tumor material and biopsy material, after removal of the tissue from a human or animal body by surgery, the process comprising in the given order the steps of:
  a) transferring the tissue to be preserved into a container;
  b) placing the container with the tissue to be preserved inside a vacuum chamber;
  c) creating a vacuum inside the container;
  d) providing a protective atmosphere in the container, by introducing a protective gas mixture directly into the container via a nozzle in the vacuum chamber, wherein the protective gas mixture surrounds the tissue;
  e) sealing the container comprising the tissue to be preserved and keeping substantially all the protective gas atmosphere within the container; and
  f) storing the container comprising the tissue to be preserved.

2. The process according to claim 1, wherein said container is a plastic bag.

3. The process according to claim 1, wherein the vacuum creation inside the container is carried out by reducing the pressure to below 100 mbar (10 kPa).

4. The process according to claim 3, wherein the pressure is reduced to a value within the range of 30 to 0 mbar (3-0 kPa).

5. The process according to claim 1, wherein the protective atmosphere comprises a medical gas mixture.

6. The process according to claim 5, wherein said medical gas mixture is an $N_2/CO_2$ gas.

7. The process according to claim 1, wherein the sealed container containing the tissue is stored under refrigerator conditions during a time period of a few hours to up to one week.

8. The process according to claim 1, wherein the tissue is stored for a histopathology procedure, transplantation, transport to a laboratory, or preservation by refrigeration.

* * * * *